(12) United States Patent
Blacker

(10) Patent No.: US 10,994,102 B2
(45) Date of Patent: May 4, 2021

(54) METHOD AND APPARATUS FOR LOADING A GUIDEWIRE INTO A CONNECTOR WITH A VALVE

(71) Applicant: Corindus, Inc., Waltham, MA (US)

(72) Inventor: Steven J. Blacker, Framingham, MA (US)

(73) Assignee: Corindus, Inc., Waltham, MA (US)

( * ) Notice: Subject to any disclaimer, the term of this patent is extended or adjusted under 35 U.S.C. 154(b) by 586 days.

(21) Appl. No.: 15/429,985

(22) Filed: Feb. 10, 2017

(65) Prior Publication Data

US 2018/0229008 A1 Aug. 16, 2018

(51) Int. Cl.
*A61M 25/09* (2006.01)
*A61M 39/10* (2006.01)
*A61M 39/06* (2006.01)
*A61B 34/00* (2016.01)

(52) U.S. Cl.
CPC ....... *A61M 25/09041* (2013.01); *A61B 34/00* (2016.02); *A61M 39/06* (2013.01); *A61M 39/10* (2013.01)

(58) Field of Classification Search
CPC ...... A61B 25/09041; A61B 2025/1081; A61B 2025/09116; A61B 2017/00469; A61M 2039/066; A61M 2039/0633
See application file for complete search history.

(56) References Cited

U.S. PATENT DOCUMENTS

| | | |
|---|---|---|
| 3,559,643 A | 2/1971 | Pannier et al. |
| 3,769,975 A | 11/1973 | Nimoy et al. |
| 4,498,902 A | 2/1985 | Ash et al. |
| 4,850,975 A | 7/1989 | Furukawa |
| 4,988,356 A * | 1/1991 | Crittenden ........ A61M 25/0169 600/434 |
| 5,279,590 A | 1/1994 | Sinko et al. |
| 5,415,639 A | 5/1995 | VandenEinde et al. |
| 5,454,785 A | 10/1995 | Smith |
| 5,484,419 A * | 1/1996 | Fleck ................. A61M 25/0113 604/171 |
| 6,110,146 A * | 8/2000 | Berthiaume .... A61M 25/09041 604/103 |
| 6,997,908 B2 | 2/2006 | Carrillo et al. |
| 8,850,676 B2 | 10/2014 | Schmitt |
| 2004/0210194 A1* | 10/2004 | Bonnette ................ A61B 17/22 604/167.06 |

(Continued)

*Primary Examiner* — Manuel A Mendez
*Assistant Examiner* — Justin L Zamory

(57) ABSTRACT

A method for loading a guidewire into a connector using a guidewire introducer includes inserting a guidewire introducer into a proximal end of a connector, the guidewire introducer having a proximal end, a distal end and a slit along the length of the guidewire introducer between the proximal end and the distal end. The guidewire introducer is advanced past a valve in the proximal end of the connector. A distal end of a guidewire is inserted into the proximal end of the guidewire introducer and advanced through the guidewire introducer and through the y-connector. The guidewire introducer is removed from the connector so that the distal end of the guidewire introducer is outside of the y-connector and proximate to the proximal end of the connector. The guidewire introducer is removed from the guidewire using the slit in the guidewire introducer.

20 Claims, 12 Drawing Sheets

(56) References Cited

U.S. PATENT DOCUMENTS

| | | | |
|---|---|---|---|
| 2005/0197663 A1* | 9/2005 | Soma | A61M 25/09 606/108 |
| 2007/0149946 A1 | 6/2007 | Viswanathan et al. | |
| 2008/0146999 A1* | 6/2008 | Tanaka | A61M 25/10 604/96.01 |

* cited by examiner

METHOD AND APPARATUS FOR LOADING A GUIDEWIRE INTO A CONNECTOR WITH A VALVE

FIELD OF THE INVENTION

The present invention relates generally to the field of catheter systems for performing therapeutic procedures and, in particular, to a method and apparatus for loading a guidewire into a connector with a valve.

BACKGROUND OF THE INVENTION

Catheters may be used for many medical procedures, including inserting a guidewire, delivering a stent and delivering and inflating a balloon. Catheterization procedures are commonly performed for diagnosis and treatment of diseases of the heart and vascular systems. The catheterization procedure is generally initiated by inserting a guidewire into a blood vessel in the patient's body. The guidewire is then advanced to the desired location, most commonly in one of the heart vessels or elsewhere in the vascular system. At this point, a catheter is slid over the guidewire into the blood vessel and/or heart. In some procedures, the catheter is a balloon catheter or stent delivery system that when deployed at the site of the lesion allows for increased blood flow through the portion of the coronary artery that is affected by the lesion.

For manual insertion of a guidewire, the physician applies torque and axial push force on the proximal end of a guidewire to effect tip direction and axial advancement at the distal end. Robotic catheter procedure systems have been developed that may be used to aid a physician in performing a catheterization procedure such as a percutaneous coronary intervention (PCI). The physician uses a robotic system to precisely steer a coronary guidewire, balloon catheter or stent delivery system in order to, for example, widen an obstructed artery. While observing the coronary anatomy using fluoroscopy, the physician manipulates a device, for example a guidewire, in order to direct the device into the appropriate vessels toward the lesion. A robotic catheter procedure system includes drive mechanisms to drive various elongated medical devices (e.g., guidewire, guide catheter, working catheter) used in catheterization procedures to provide linear and rotational movement of the elongated medical device.

During one type of catheter procedure, a guide catheter is inserted into either a patient's femoral or radial artery through an introducer and the guide catheter is positioned proximate the coronary ostium of the patient's heart. During the procedure, the guide catheter is used to guide other elongated medical devices such as a guidewire or a balloon catheter into a patient. Typically, the end of the guide catheter not inserted into the patient is connected to a connector, such as a y-connector, with a valve (e.g., a hemostasis valve) to allow introduction of an elongated medical device and a contrast agent or medicine into a lumen of the guide catheter. For example, a first leg of the y-connector may be configured to receive a guidewire or other elongated medical device and a second leg of the y-connector may be configured to allow introduction of a contrast agent or medicine. The first leg of a y-connector may also include a valve that permits insertion or removal of the guidewire or other elongated medical device but prohibits fluids from exiting the first leg. A guidewire may have a flexible or floppy end which can be difficult to insert past the valve in the connector. It would be desirable to provide an apparatus and method for loading a guidewire into a connector that allows the flexible end of the guidewire to advance past a valve in the connector and that allows the guidewire introducer to be removed proximate to the connector without having to thread the guidewire introducer off the entire length of the guidewire to the proximal end of the guidewire.

SUMMARY OF THE INVENTION

In accordance with an embodiment, a method for loading a guidewire into a connector using a guidewire introducer includes inserting a guidewire introducer into a proximal end of a connector, the guidewire introducer having a proximal end, a distal end and a slit along the length of the guidewire introducer between the proximal end and the distal end, advancing the guidewire introducer past a valve in the proximal end of the connector, inserting a distal end of a guidewire into the proximal end of the guidewire introducer, advancing the guidewire through the guidewire introducer and through the connector, removing the guidewire introducer from the connector so that the distal end of the guidewire introducer is outside of the connector and proximate to the proximal end of the connector and removing the guidewire introducer from the guidewire using the slit in the guidewire introducer.

In accordance with another embodiment, a guidewire introducer for loading a guidewire into a connector with a valve includes a body having a length, a proximal end and a distal end, a slit having a spiral configuration along the length between the proximal end and the distal end and a tapered portion at the proximal end.

In accordance with another embodiment, a guidewire introducer for loading a guidewire into a connector with a valve includes a body having a length, a proximal end and a distal end, a slit having a zig-zag configuration along the length between the proximal end and the distal end and a tapered portion at the proximal end.

BRIEF DESCRIPTION OF THE DRAWINGS

This application will become more fully understood from the following detailed description, taken in conjunction with the accompanying figures, wherein like reference numerals refer to like elements in which.

DETAILED DESCRIPTION OF THE PREFERRED EMBODIMENTS

Figure 1:
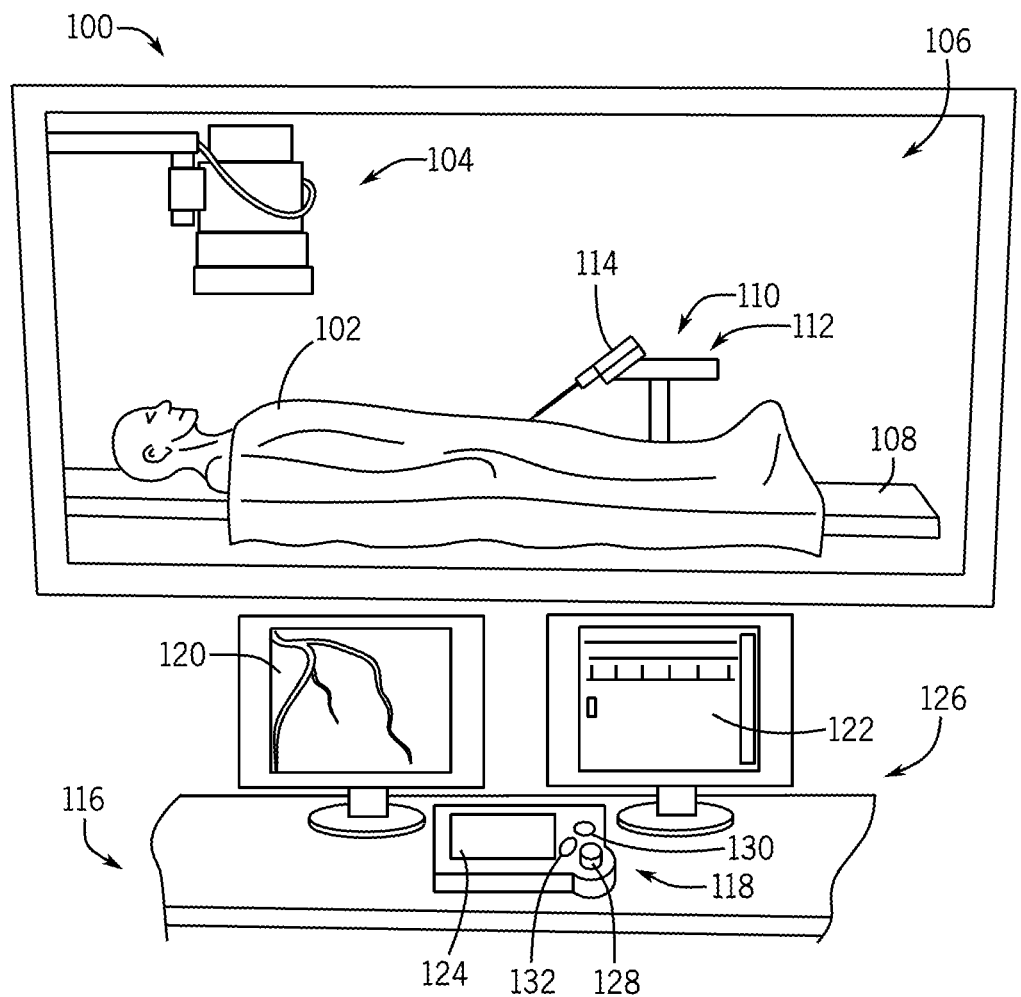
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guidewire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 described herein are explained primarily in relation to the treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guidewires, guide catheters, working catheters such as balloon catheters and stent delivery systems, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a drive assembly 114 (e.g., that may contain a sterile, disposable portion) supported by a robotic arm 112 which may be used to automatically advance a guidewire or working catheter into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guidewire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Drive assembly 114 includes various drive mechanisms to cause movement (e.g., axial and rotational movement) of the components of the bedside system 110 including the percutaneous devices.

In one embodiment, controls 118 include a touch screen 124, one or more joysticks 128 and buttons 130, 132. The joystick 128 may be configured to advance, retract, or rotate various components and percutaneous devices such as, for example, a guidewire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guidewire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with a controller of the system (e.g., located in workstation 116 or in communication with workstation 116). In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guidewire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

As used herein, the direction distal is the direction toward the patient and the direction proximal is the direction away from the patient. The terms up and upper refer to the general direction away from the direction of gravity and the terms bottom, lower and down refer to the general direction of gravity.

Figure 2:
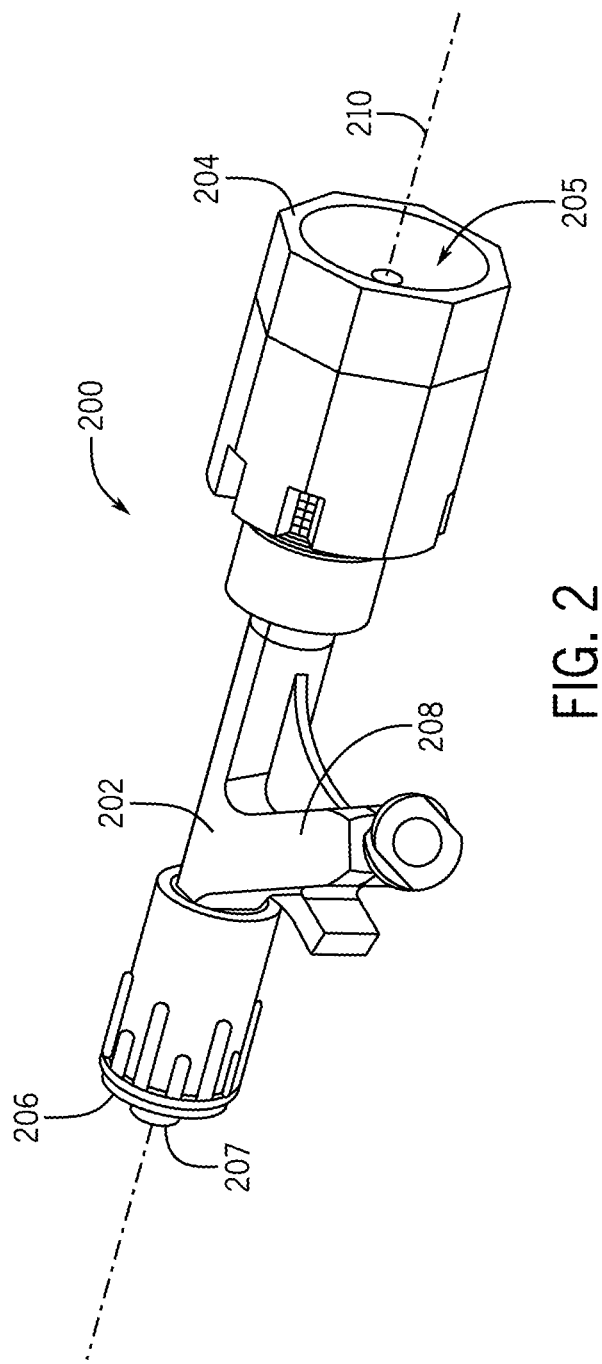
FIG. 2 is a perspective view of an exemplary y-connector in accordance with an embodiment.

Bedside system 110 of catheter procedure system 100 may include a connector that may be in communication with a guide catheter, guidewire and a working catheter. The connector includes a valve, e.g., a hemostasis valve. The following description discusses embodiments with respect to a y-connector, however, it should be understood that the connector may be any other type of connector including a valve such as a straight connector (e.g., a connector with a single leg). FIG. 2 is a perspective view of an exemplary y-connector in accordance with an embodiment. In one embodiment, y-connector 200 is a hemostasis valve. Y-connector 200 includes a valve body with a first leg 202 having a proximal end 204, a distal end 206 and a lumen extending between the proximal end 204 and the distal end 206. A proximal port or opening 205 is adjacent to the proximal end 204 and a distal port or opening 207 is adjacent the distal end 206. The first leg 202 defines a longitudinal axis 210 extending from the proximal end 204 of the first leg 202 to the distal end 206 of the first leg 202. The y-connector 200 also includes a second leg 208 that is angled away from the longitudinal axis 210 defined by the first leg 202. The second leg 208 includes an internal lumen and is in fluid communication with the lumen of the first leg 202.

The first leg 202 of y-connector 200 includes a valve adjacent to the proximal end 204 that permits insertion and removal of a percutaneous device such as a guidewire or working catheter into the y-connector 200 and prohibits fluids from exiting the proximal end 204 of the first leg 202. In one embodiment, the valve may be a bleed-back valve that may be used to reduce the blood that may be lost during an interventional procedure. The bleed-back valve acts to allow an elongated device such as a guidewire to extend therethrough but minimizes blood loss through the valve. In another embodiment, the proximal end 204 of the first leg 202 may include a Tuohy Borst adapter. Tuohy Borst adapters are known in the art and operate to adjust the size of the opening 205 in the proximal end 204 of the first leg 202 of the y-connector 200 to minimize the risk that fluids may exit the proximal end 204 of the first leg 202. For example, a Tuohy Borst adapter may be used to adjust the size of the opening to zero to stop flow of fluid or may be used to adjust to opening to hold onto or fixate an elongated medical device (e.g., a guidewire) that is passing through it. In another embodiment, the connector (e.g., y-connector 200) may include both a bleed-back valve and a Tuohy Borst adapter. Other types of adapters known in the art may be used with the y-connector 200 to adjust the size of the opening 205 in the proximal end 204 of the first leg 202.

Figure 3:
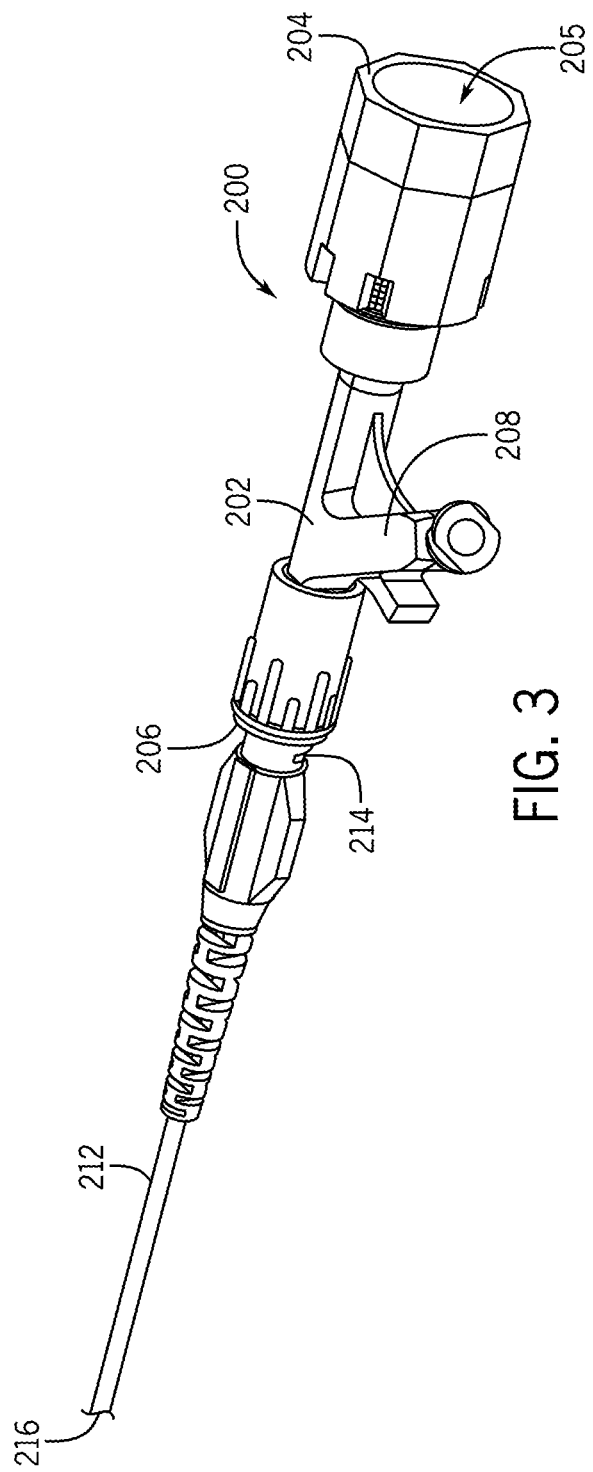
FIG. 3 is a perspective view of a y-connector and guide catheter in accordance with an embodiment.

The distal end 206 of the first leg 202 may be connected to a guide catheter as shown in FIG. 3. In FIG. 3, a guide catheter 212 has a proximal end 214 and a distal end 216. The proximal end 214 of the guide catheter 212 is attached to the distal end 206 of the first leg 202 of the y-connector 200. In one embodiment, the distal end 206 of the first leg 202 is attached to the proximal end 214 of the guide catheter 212 such that the central lumen of y-connector 200 is in fluid communication with the central lumen of the guide catheter 212. The second leg 208 of the y-connector 200 provides a port for the introduction of fluids (e.g., contrast media, medicine, etc.) into the lumen of the guide catheter 212. An elongated medical device such as a guidewire or working catheter may be advanced into the guide catheter 212 through the y-connector 200. For example, a guidewire (not shown) may be inserted into the proximal end 204 of the first leg 202 and through the first leg 202 of the y-connector 200 into the lumen of the guide catheter 212.

Figure 4:
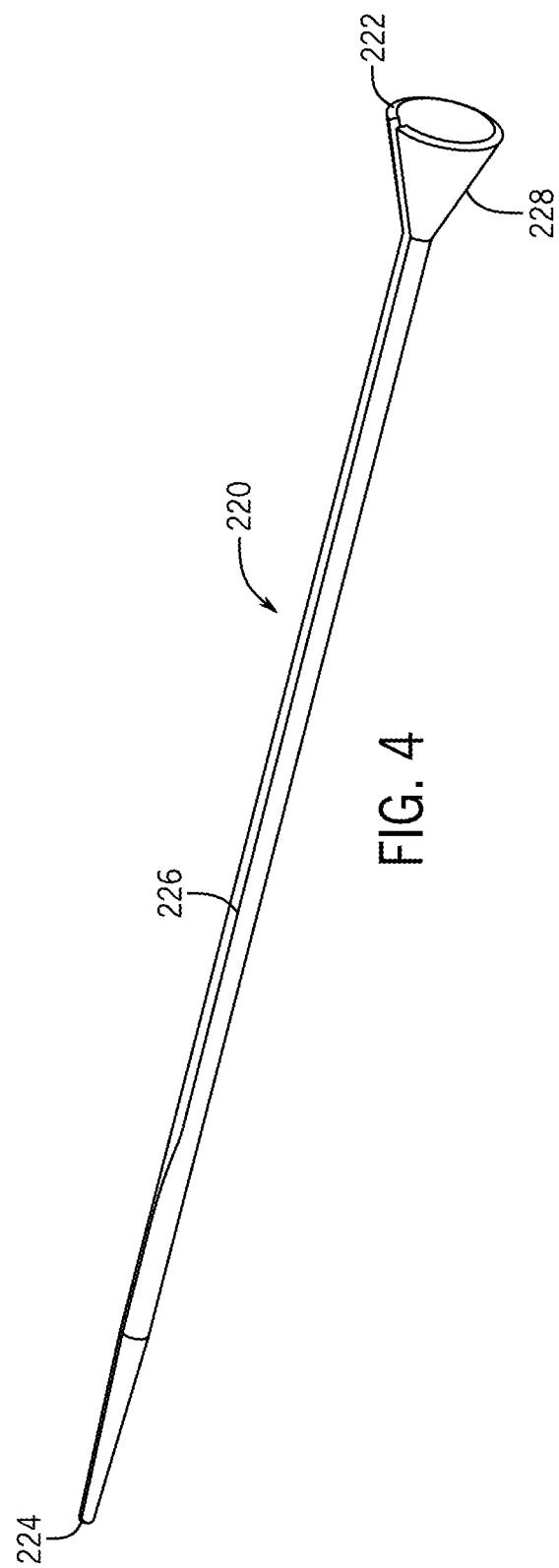
FIG. 4 is a perspective view of a guidewire introducer with a lengthwise slit in accordance with an embodiment.

A guidewire introducer may be used to facilitate insertion of a guidewire into the y-connector and past the valve in the proximal end of the first leg of the y-connector. FIG. 4 is a perspective view of a guidewire introducer with a lengthwise slit in accordance with an embodiment. The guidewire introducer 220 includes a proximal end 222 and a distal end 224. The proximal end 222 includes a tapered portion 228 to allow insertion of a guidewire into the proximal end 222 of the guidewire introducer 220. The guidewire introducer 220 also includes a slit 226 that is continuous along the entire length of the guidewire introducer 220 between the proximal end 222 and the distal end 224. In one embodiment, the guidewire introducer 220 has sufficient rigidity to allow the guidewire introducer 220 to go through the valve and create a passageway to allow the guidewire introducer to go through the valve and create a passageway to allow a guidewire to get past the valve without collapsing or damaging the distal tip of the guidewire. In one embodiment, the slit 226 may be configured to close when it is inserted in the valve in a manner such as a spring pin or to close and overlap itself in a manner such as a coiled spring pin and then open again when removed from the valve. For example, the compliance of the material used to construct the guidewire introducer 220 may be selected to allow the slit 226 to close or to overlap itself when the guidewire introducer 220 is inserted into the valve and to allow the slit 226 to spring open when the guidewire introducer 220 is removed from the valve. The slit 226 may have a width that is similar to the width of the guidewire, smaller than the guidewire or larger than the guidewire.

Figure 5:
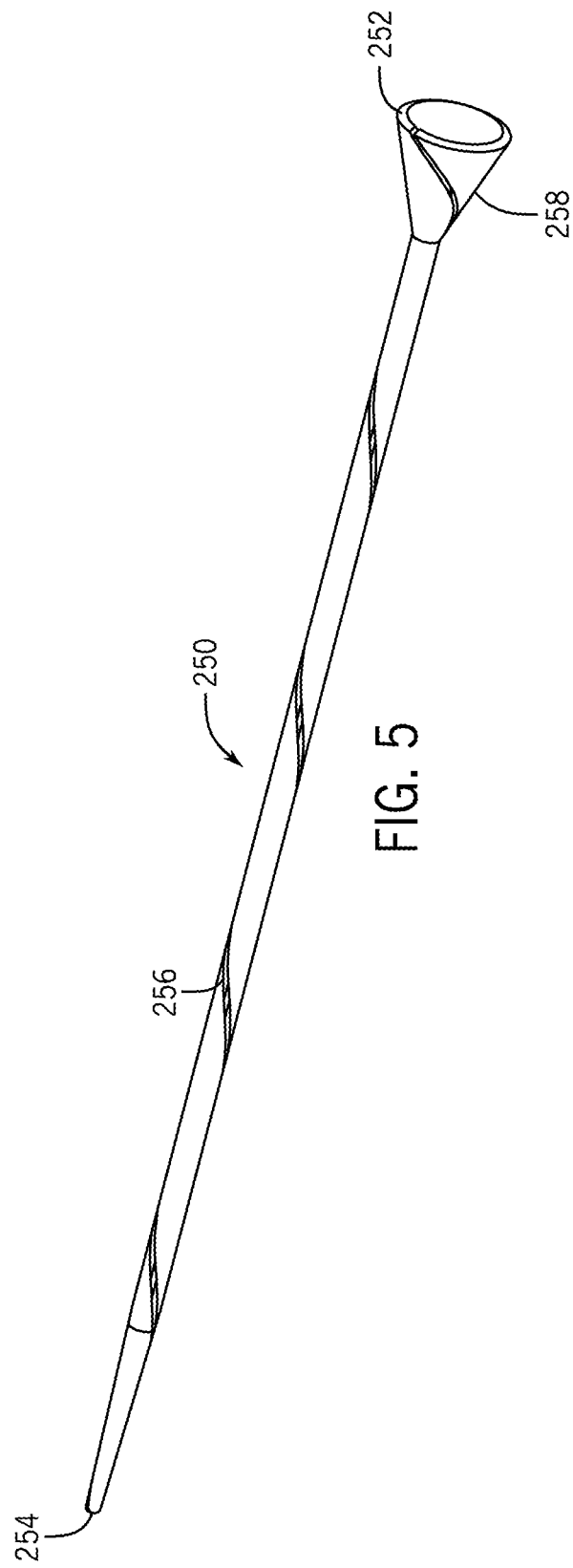
FIG. 5 is a perspective view of a guidewire introducer with a spiral slit in accordance with an embodiment.
Figure 6:
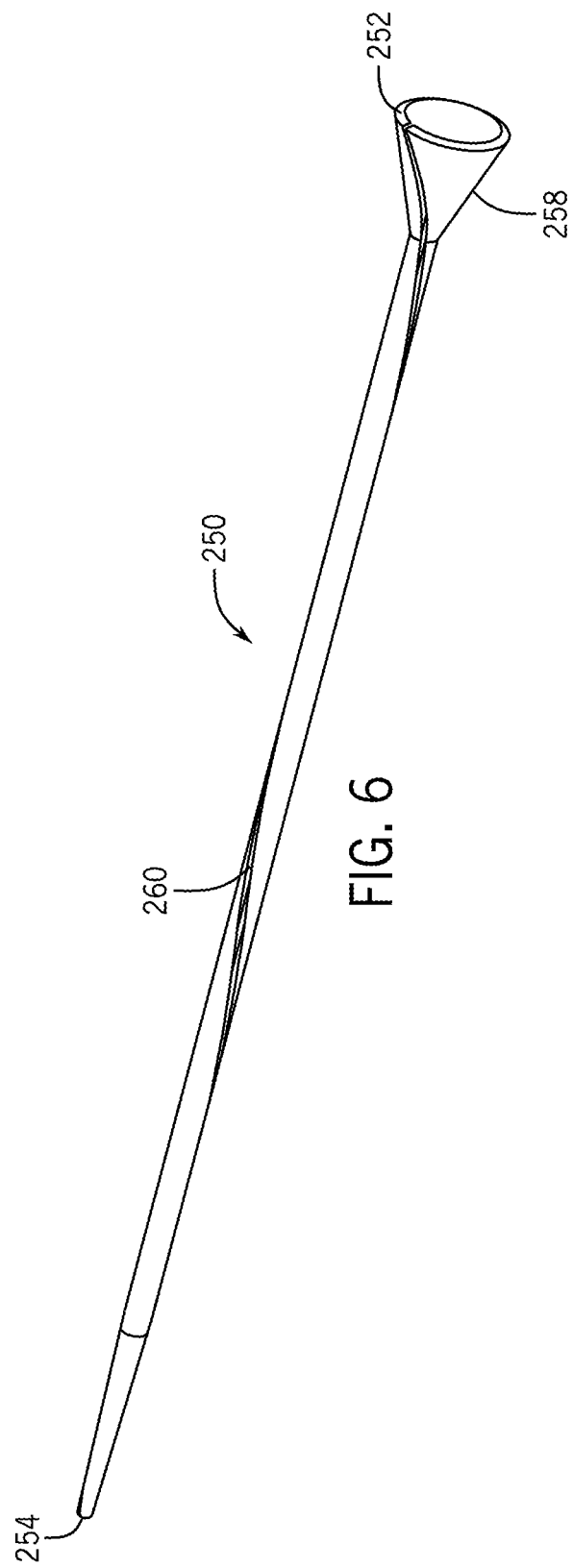
FIG. 6 is a perspective view of a guidewire introducer with a spiral slit in accordance with an embodiment.

As discussed further below, the slit 226 may be used to remove the guidewire introducer 220 from over a guidewire without requiring the guidewire introducer 220 be slid or threaded over the length of the guidewire to a proximal end of the guidewire. In an embodiment, the proximal end 222 of the guidewire introducer 220 may include a tab (not shown) that may be used to remove (e.g., pull the introducer off of a guidewire). The tab (not shown) may be positioned on the tapered portion 228 opposite the slit 226. In another embodiment, the guidewire introducer with slit includes a spiral slit along the length of the guidewire introducer as shown in FIGS. 5 and 6. In FIG. 5, the guidewire introducer 250 includes a proximal end 252 and a distal end 254. The proximal end 2532 includes a tapered portion 258 to allow insertion of a guidewire into the proximal end 252. A slit 256 is provided along the length of the guidewire introducer 250 between the proximal end 252 and the distal end 254. The slit 256 is in a spiral configuration along the length of the guidewire introducer 250. In FIG. 6, an alternative spiral configuration of a slit 260 along the length of the guidewire introducer 250 is shown. In another embodiment, the slit along the length of the guidewire introducer between the proximal end and the distal end may be a zig-zag configuration. In yet another embodiment, the slit may be straight along a portion of the length of the guidewire introducer (e.g., proximate the proximal end) and then a spiral or zig-zag configuration along the remaining portion of the length of the guidewire introducer towards the distal end.

Figure 7:
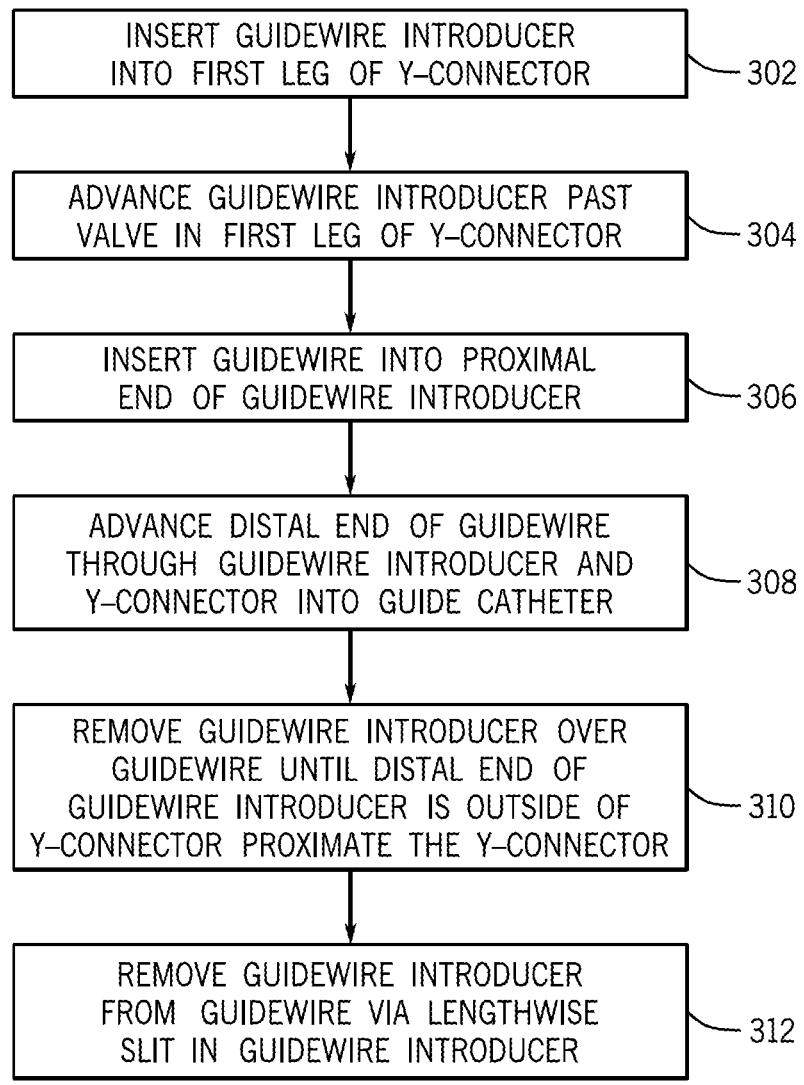
FIG. 7 illustrates a method for loading a guidewire into a connector in accordance with an embodiment.
Figure 8:
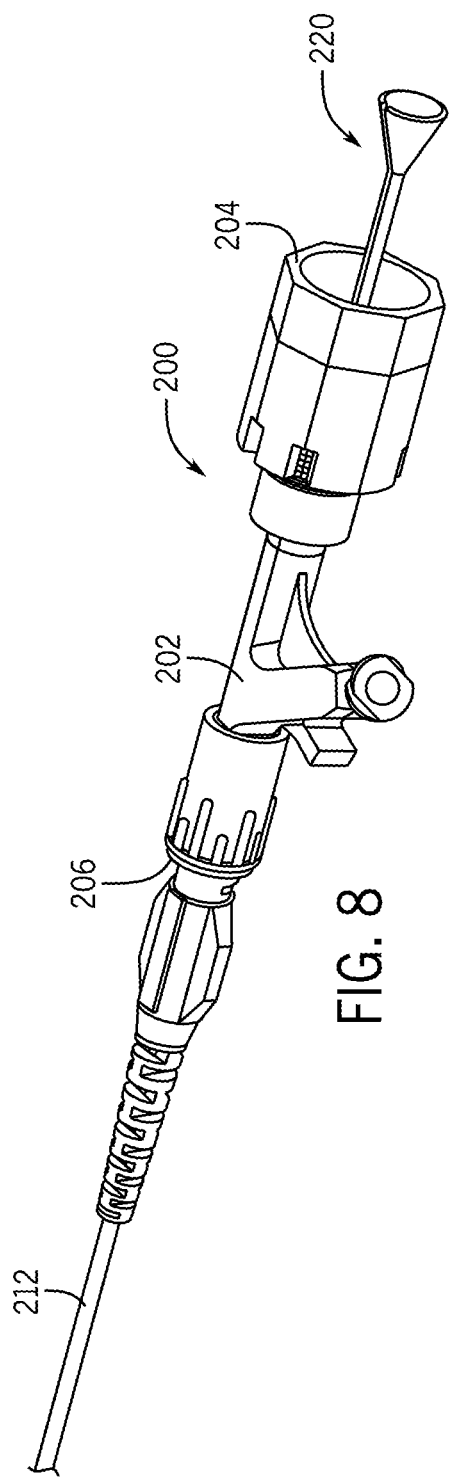
FIG. 8 is a perspective view of a guidewire introducer positioned within a y-connector in accordance with an embodiment.

The following description of FIGS. 7-12 discusses embodiments with respect to a y-connector, however, it should be understood that the connector may be any other type of connector including a valve (e.g., a hemostasis valve) such as a straight connector (e.g., a connector with a single leg). FIG. 7 illustrates a method for loading a guidewire into a connector in accordance with an embodiment. At block 302, a guidewire introducer with a slit is inserted into the proximal end of the first leg of the y-connector. At block 304, the guidewire introducer is advanced past the valve in the proximal end of the first leg of the y-connector and towards the distal end of the first leg of the y-connector. FIG. 8 is a perspective view of a guidewire introducer positioned within a y-connector in accordance with an embodiment. In FIG. 8, the guidewire introducer 220 is shown after insertion into the proximal end 204 of first leg 202 of the y-connector 200. The guidewire introducer 220 is advanced through the first leg 202 past the valve in the proximal end 204 and towards the distal end 206 of the first leg 202.

Figure 9:
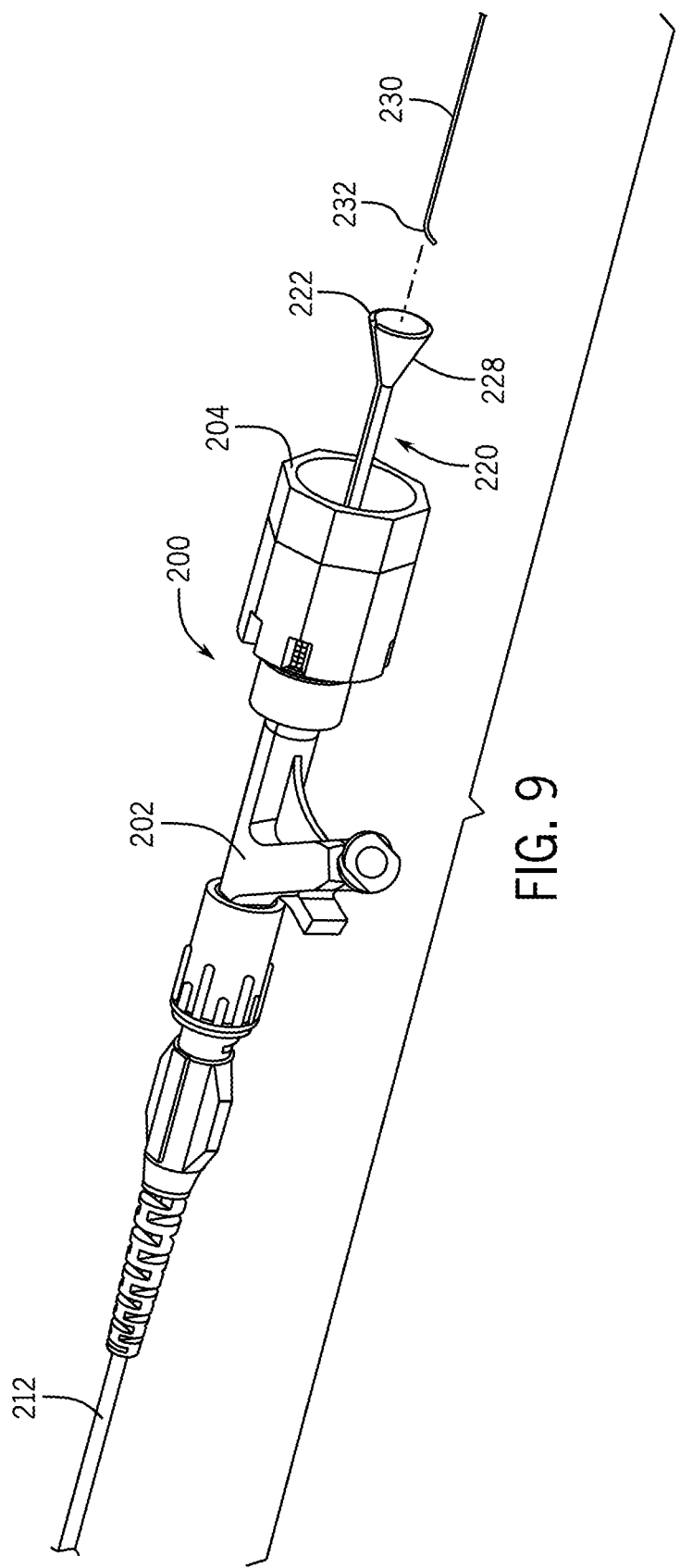
FIG. 9 is a perspective view of a y-connector, guide catheter, guidewire introducer and guidewire in accordance with an embodiment.
Figure 10:
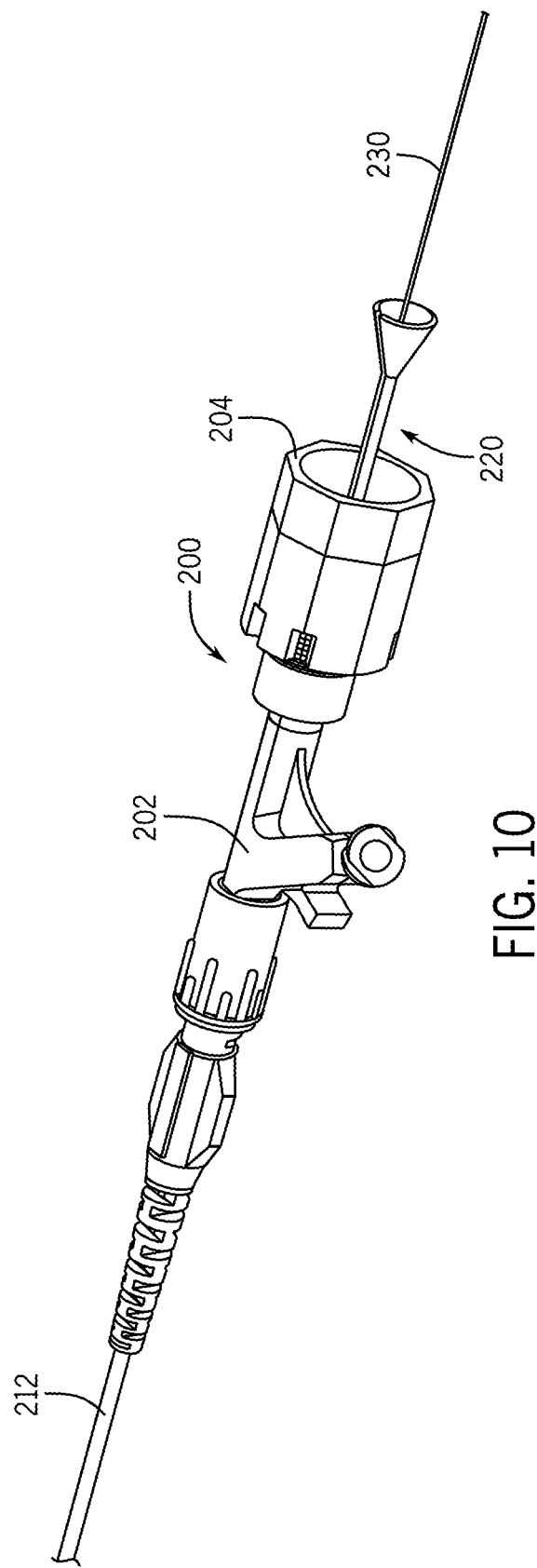
FIG. 10 is a perspective view of a guidewire positioned within a guidewire introducer in accordance with an embodiment.

Returning to FIG. 7, at block 306, a distal end of a guidewire is inserted into the proximal end of the guidewire introducer. FIG. 9 is a perspective view of a y-connector, guide catheter; guidewire introducer and guidewire in accordance with an embodiment. In FIG. 9, a guidewire 230 includes a distal end 232 that may be inserted into the proximal end 222 of the guidewire introducer 220. In one embodiment, the distal end 232 of the guidewire may be flexible or bendable to put a curve at the tip. In another embodiment, the distal end of the guidewire may be pre-shaped with a curve. Returning to FIG. 7, at block 308, the distal end of the guidewire is advanced through the guidewire introducer and y-connector into the guide catheter. FIG. 10 is a perspective view of a guidewire positioned within a guidewire introducer in accordance with an embodiment. In FIG. 10, the guidewire 230 is shown after the distal end has been inserted into the guidewire introducer 220 and through the y-connector 200 into the guide catheter 212. The guidewire introducer 220 facilitates advancement of the distal end 232 (shown in FIG. 9) of the guidewire 230 past the valve in the proximal end 204 of the first leg 202 of the y-connector 200.

Figure 11:
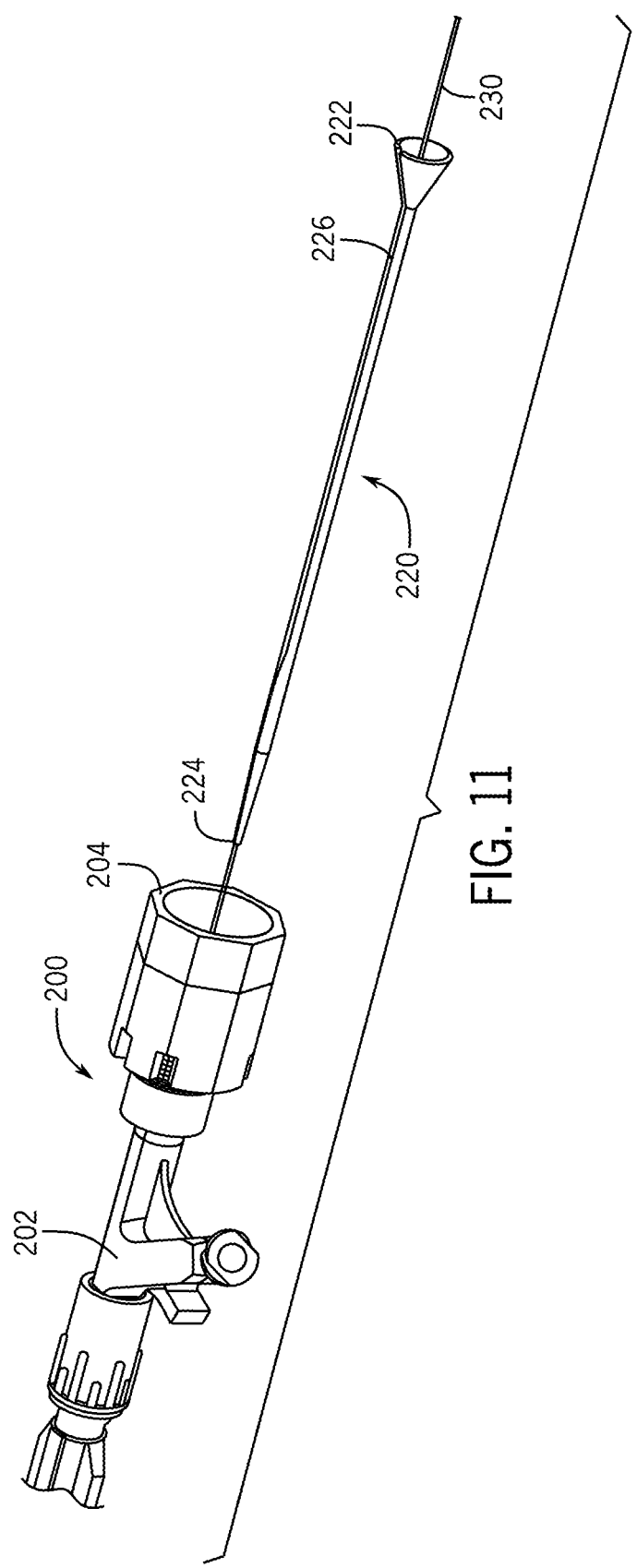
FIG. 11 is a perspective view of a y-connector, guide catheter, guidewire introducer and guidewire in accordance with an embodiment.
Figure 12:
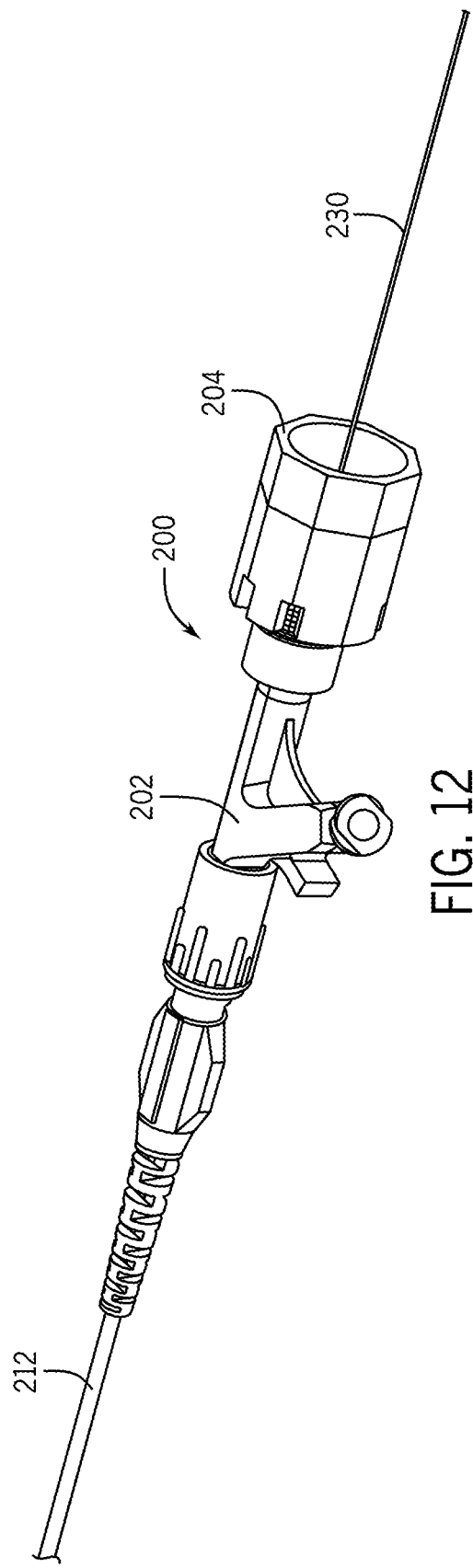
FIG. 12 is a perspective view of a y-connector, guide catheter and guidewire in accordance with an embodiment.

Returning to FIG. 7, at block 310 once the guidewire is advanced into the guide catheter, the guidewire introducer is removed from the y-connector over the guidewire until the distal end of the guidewire introducer is outside of the y-connector and proximate to the proximal end of the y-connector. FIG. 11 is a perspective view of a y-connector, guide catheter, guidewire introducer and guidewire in accordance with an embodiment. In FIG. 11, the guidewire introducer 220 is shown after removal from the y-connector 200. The guidewire introducer 220 is positioned over the guidewire and the distal end 224 of the guidewire introducer 220 is proximate to the proximal end 204 of the y-connector 200. Returning to FIG. 7, at block 312, the guidewire introducer is removed from the guidewire via the lengthwise slit 226 (shown in FIG. 11) in the guidewire introducer. FIG. 12 is a perspective view of a y-connector, guide catheter and guidewire in accordance with an embodiment. In FIG. 12, the guidewire introducer has been removed and the guidewire 230 is positioned in the y-connector 200 and guide catheter 212. Referring to FIG. 4 and FIG. 11 The guidewire introducer includes a first tapered portion proximate the proximal end 222 and a second tapered portion proximate the distal end 224, the diameter of the first tapered portion decreasing from the proximal end 222 toward the distal end 224 and the diameter of the second tapered portion decreasing from a region proximal the distal end 224 of the second tapered portion toward the distal end 224 of the second tapered portion.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

What is claimed is:

1. A method for loading a guidewire into a connector using a guidewire introducer, the method comprising:
    inserting a guidewire introducer into a proximal end of a connector, the guidewire introducer having a proximal end, a distal end and a slit along the entire length of the guidewire introducer between the proximal end and the distal end;
    advancing the guidewire introducer past a valve in the proximal end of the connector, wherein the guidewire introducer is sufficiently rigid to create a passageway to allow the guidewire introducer to get past the valve without collapsing and wherein the slit closes when the guidewire introducer is inserted into the valve;
    inserting a distal end of a guidewire into the proximal end of the guidewire introducer;
    advancing the guidewire through the guidewire introducer and through the connector;

removing the guidewire introducer from the connector so that the distal end of the guidewire introducer is outside of the connector and proximate to the proximal end of the connector; and removing the guidewire introducer from the guidewire using the slit in the guidewire introducer without requiring the guidewire introducer to be slid or threaded over the length of the guidewire to a proximal end of the guidewire.

2. A method according to claim 1, wherein the proximal end of the guidewire introducer is tapered.

3. A method according to claim 1, wherein the connector includes a distal end and the distal end is connected to a guide catheter.

4. A method according to claim 1, wherein advancing the guidewire through the guidewire introducer and through the connector further comprises advancing the guidewire into the guide catheter.

5. A method according to claim 1, wherein the distal end of the guidewire is flexible.

6. A method according to claim 1, wherein the valve in the connector is selected from a group of valves consisting of a hemostasis valve, a bleed-back valve and a portion of a Tuohy Borst adapter.

7. A method according to claim 1, wherein the slit has a spiral configuration along the length of the guidewire introducer.

8. A method according to claim 1, wherein at least a portion of the slit springs open when the guidewire introducer is removed from the valve.

9. A method according to claim 1, wherein the guidewire introducer is formed of a material having sufficient compliance to allow the slit to close when the guidewire introducer is inserted into the valve.

10. A method according to claim 1, wherein the slit overlaps itself in response to insertion of the guidewire introducer into the valve.

11. The method according to claim 1, wherein the guidewire introducer includes a first tapered portion proximate the proximal end and a second tapered portion proximate the distal end, the diameter of the first tapered portion decreasing from the proximal end toward the distal end and the diameter of the second tapered portion decreasing from the proximal distal end of the second tapered portion toward the distal end of the second tapered portion.

12. The method of claim 1, wherein portions of the slit are open, with opposing edges of the portions of the slit being spaced apart and out of mutual contact, prior to the inserting of the guidewire introducer into a proximal end of the connector and wherein positioning of the guidewire introducer into the valve results in the portions of the slit closing.

13. The method of claim 12, wherein the slit closes by overlapping itself in response to insertion of the guidewire introducer into the valve.

14. The method of claim 12, wherein the opposing edges of the portions of the slit are spaced apart by width greater than or equal to a width of the guidewire prior to the inserting of the guidewire introducer into the proximal end of the connector.

15. The method of claim 12, wherein the valve constricts the portions of the slit to close the slit during introduction of the portions of the slit into the valve.

16. The method of claim 12, wherein the slit closes by overlapping itself in response to insertion of the guidewire introducer into the valve.

17. A method for loading a guidewire into a connector using a guidewire introducer, the method comprising:
inserting a guidewire introducer into a proximal end of a connector, the guidewire introducer having a proximal end, a distal end and a slit along the entire length of the guidewire introducer between the proximal end and the distal end, wherein the proximal end of the introducer has a tapered;

advancing the guidewire introducer past a valve in the proximal end of the connector;

inserting a distal end of a guidewire into the proximal end of the guidewire introducer;

advancing the guidewire through the guidewire introducer and through the connector;

removing the guidewire introducer from the connector so that the distal end of the guidewire introducer is outside of the connector and proximate to the proximal end of the connector; and removing the guidewire introducer from the guidewire using the slit in the guidewire introducer without requiring the guidewire introducer to be slid or threaded over the length of the guidewire to a proximal end of the guidewire.

18. The method of claim 17, wherein the tapered portion extends from the outermost periphery of the proximal end.

19. A method for loading a guidewire into a connector using a guidewire introducer, the method comprising:
inserting a guidewire introducer into a proximal end of a connector, the guidewire introducer having a proximal end, a distal end and a slit along the entire length of the guidewire introducer between the proximal end and the distal end;

advancing the guidewire introducer past a valve in the proximal end of the connector;

inserting a distal end of a guidewire into the proximal end of the guidewire introducer;

advancing the guidewire through the guidewire introducer and through the connector;

removing the guidewire introducer from the connector so that the distal end of the guidewire introducer is outside of the connector and proximate to the proximal end of the connector; and removing the guidewire introducer from the guidewire using the slit in the guidewire introducer without requiring the guidewire introducer to be slid or threaded over the length of the guidewire to a proximal end of the guidewire, wherein side edges of the slit move relative to one another in response to insertion of the guidewire introducer into the valve.

20. The method of claim 19, wherein the side edges mover away from one another in opposite directions in response to insertion of the guidewire introducer into the valve.

* * * * *